(12) United States Patent
Kunz

(10) Patent No.: US 10,543,633 B2
(45) Date of Patent: Jan. 28, 2020

(54) INJECTION MOLDING DEVICE COMPRISING MOVABLE STRIPPERS

(71) Applicant: Braun GmbH, Kronberg (DE)

(72) Inventor: Marc Kunz, Goergeshausen (DE)

(73) Assignee: BRAUN GMBH, Kronberg (DE)

( * ) Notice: Subject to any disclaimer, the term of this patent is extended or adjusted under 35 U.S.C. 154(b) by 273 days.

(21) Appl. No.: 15/197,246

(22) Filed: Jun. 29, 2016

(65) Prior Publication Data

US 2017/0001352 A1    Jan. 5, 2017

(30) Foreign Application Priority Data

Jun. 30, 2015   (EP) ..................... 15174563
Apr. 13, 2016   (EP) ..................... 16165008

(51) Int. Cl.
B29C 45/40    (2006.01)
B29C 45/16    (2006.01)
B29L 31/34    (2006.01)

(52) U.S. Cl.
CPC ...... B29C 45/4005 (2013.01); B29C 45/1628 (2013.01); *B29C 2045/4078* (2013.01); *B29L 2031/3481* (2013.01)

(58) Field of Classification Search
CPC . B29C 45/4005; B29C 45/261; B29C 45/162; B29C 45/1628; B29C 2045/4078; B29C 2045/1629; B29C 45/36; B29L 2031/3481; B29L 2031/425; A61C 17/225
See application file for complete search history.

(56) References Cited

U.S. PATENT DOCUMENTS

| | | | |
|---|---|---|---|
| 6,322,738 B1 | 11/2001 | Sicilia et al. | |
| 2002/0014720 A1 | 2/2002 | Sicilia et al. | |
| 2004/0047933 A1* | 3/2004 | Kroeger | B29C 33/0022 |
| | | | 425/112 |
| 2010/0092711 A1 | 4/2010 | Atance Orden et al. | |
| 2012/0328814 A1 | 12/2012 | Atance Orden et al. | |
| 2017/0334093 A1* | 11/2017 | De Almeida | B29C 45/0055 |

FOREIGN PATENT DOCUMENTS

| | | |
|---|---|---|
| DE | 102010033675 | 3/2011 |
| JP | S6149808 | 11/1986 |
| JP | 2003189936 | 8/2003 |
| WO | WO2012118489 | 7/2012 |

OTHER PUBLICATIONS

European Search Report, dated Aug. 21, 2015; 9 pages.

* cited by examiner

*Primary Examiner* — Christopher T Schatz
*Assistant Examiner* — Cynthia L Schaller
(74) *Attorney, Agent, or Firm* — Vladimir Vitenberg

(57) ABSTRACT

A molding device for manufacturing a plastic hollow part by injection molding includes an injection nozzle and first and second molding stations. Each molding station has a first mold including two mold halves forming, respectively, first and second mold cavities, and a core having a first end, which can be at least partially located inside the first and second mold cavities. A first stripper can be arranged on the core in a passive position, spaced from the first end of the core at a first distance; in a molding position, spaced from the first end of the core at a second distance; and in a demolding position, spaced from the first end of the core at a third distance; wherein the first distance is greater than the second distance, and the second distance is greater than the third distance.

18 Claims, 8 Drawing Sheets

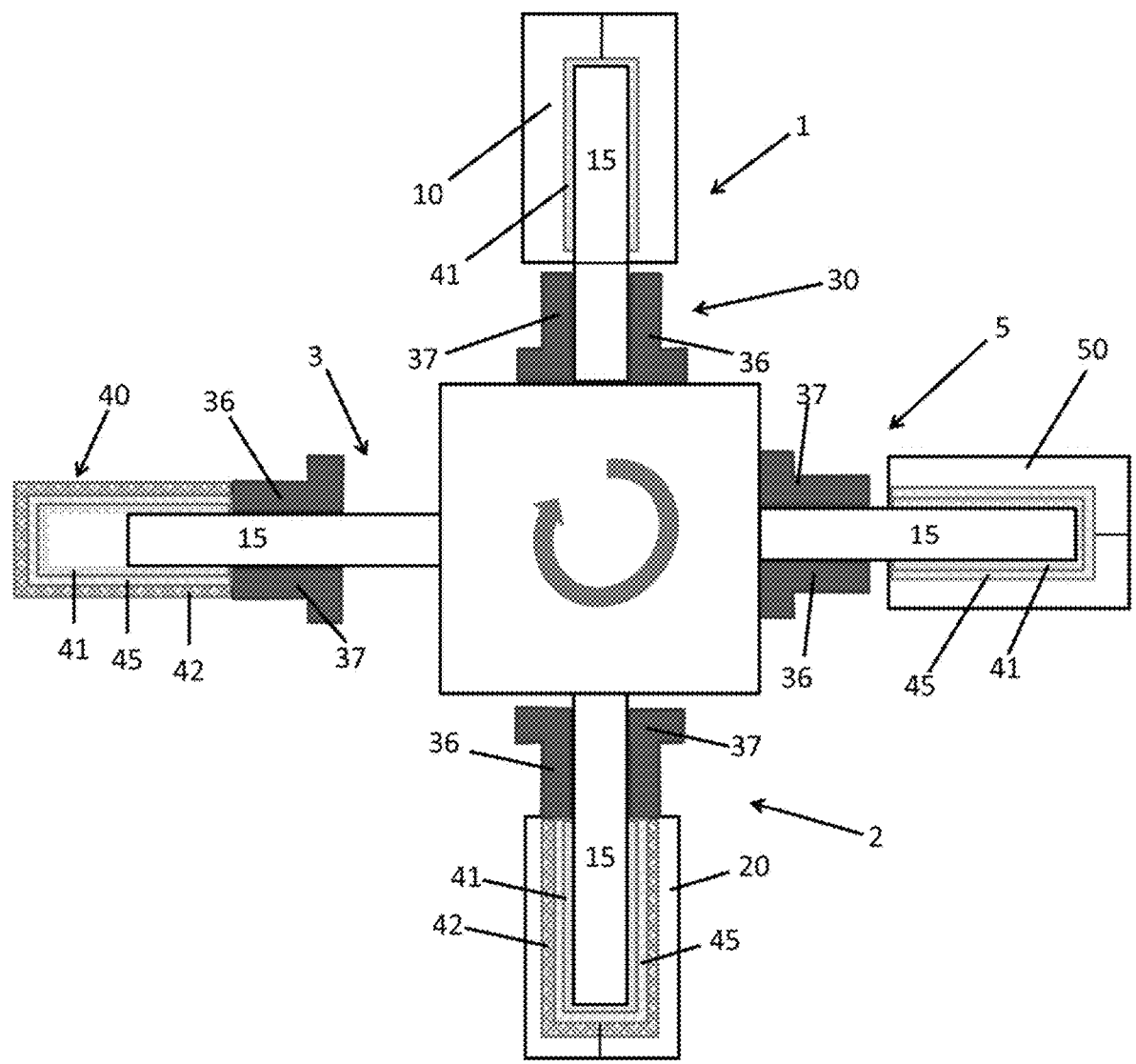

INJECTION MOLDING DEVICE COMPRISING MOVABLE STRIPPERS

FIELD OF THE INVENTION

A molding device comprising at least a movable stripper is disclosed herein wherein the molding device can be used for injection molding of hollow parts comprising at least two molding stations each comprising at least one molding cavity. A core is located at least partially in the molding cavities in order to fill the space in the cavity partially. At the surface of the core at least one movable stripper is arranged which can be arranged at least in three different positions, namely a passive position, a molding position and a demolding position. The three different positions are located at the core at different distances from the end of the core which is located inside of the molding cavities. Thereby the passive position is located at the largest distance from said end of the core. That means the distance of the molding and demolding positions to the end of the core which is located in the molding cavities is shorter than the distance in the passive position. Relative to each other the distance in the molding position is larger than the distance in the demolding position.

In addition, a method of using the molding device as described herein is disclosed in order to produce hollow parts by injection molding. Thereby, the stripper of the molding device is used as part of the mold in its molding position and used to remove the injected hollow part from the core in its demolding position.

Further, injection molded hollow parts are provided which are produced by using the molding device and/or the method as disclosed herein. The hollow parts are preferably used as housing for the motor and/or driving part of an electric toothbrush.

BACKGROUND OF THE INVENTION

Molding of hollow parts is a continuous need for plastic industry. In particular, consumer goods are usually packed into plastic hollow parts which are produced by injection molding. In addition, most of the small electronic appliances are also housed in injection molded plastic hollow parts. Thus, there exists a continuous need in industry to form plastic hollow parts of several forms and functions. Complex forms of the plastic objects require complex mold cavities. The more complex is the plastic object to be formed the more mold parts are usually needed. As a consequence molding devices become larger in order to meet the geometric requirements of the complex molds. Said problem increases if multilayer plastic objects shall be formed or undercuts are needed in the plastic object. EP0894604A1, DE102010033675A1, JP61049808A and EP2159031A1 disclose multi-layer injection molding devices with several molding stations which uses cavity extension elements in addition to mold halves for forming the mold cavities in order to combine design flexibility and multi-layer molding. Further, the pre-molded parts are transferred between the different molding stations. However, these devices are still complex. Thus, there exists a continuous need to reduce complexity of molding devices by containing the design flexibility of the molded parts. Thus, it is an object of the molding device described herein to produce complex plastic objects with minimal mold parts and small geometric dimensions.

SUMMARY OF THE INVENTION

According to one aspect a molding device for manufacturing at least a plastic hollow part by injection molding comprising at least a first molding station comprising at least a first mold comprising a first mold half and a second mold half forming a first mold cavity for molding a first part of a hollow part;

at least a second molding station comprising at least a second mold comprising a first mold half and a second mold half forming a second mold cavity for molding a second part of the hollow part;

at least a demolding station for demolding the hollow part;

wherein a core which is transferable from the first molding station to the second molding station and/or to the demolding station is locatable at least partially inside the first and second mold cavity thereby forming a part of the first and second mold cavity;

wherein at least one stripper is slidingly arranged around an outer surface of the core;

wherein the stripper is arranged at the core in a passive position spaced from a first end of the core with a first distance at the first molding station, wherein the first end of the core is located at least partially inside the first mold cavity and the stripper is located outside the first mold cavity;

wherein the stripper is arranged at the core in a molding position spaced from a first end of the core with a second distance at the second molding station, wherein the first end is located at least partially inside the second mold cavity and the stripper together with the first mold half and the second mold half of the second mold form the second mold cavity;

wherein the stripper is arranged at the core in a demolding position spaced from a first end of the core with a third distance when the core is positioned outside of the first and second mold cavity at the demolding station; and wherein the first distance is larger than the second distance and wherein the second distance is larger than the third distance.

According to another aspect a method of manufacturing a plastic hollow part by injection molding is disclosed herein, wherein the method comprises injecting a first plastic material into a first mold cavity onto a core in order to form a first part of a hollow part at a first molding station;

transferring the core together with the first part of the hollow part to a second mold comprising a first mold half and a second mold half and injecting a second plastic material into a second mold cavity onto the first part of the hollow part in order to form a second part of the hollow part at a second molding station;

transferring the core together with the hollow part to a demolding station and removing the hollow part from the core;

wherein the hollow part is removed from the core using a stripper which is arranged at the core and wherein the stripper is located outside the first mold cavity at the first molding station and wherein the stripper forms the second mold cavity together with the first mold half and the second mold half of the second mold. In particular the method of manufacturing a plastic hollow part by injection molding uses a molding device as disclosed herein.

According to another aspect a plastic hollow part is disclosed which is manufactured with a molding device and/or according to a method as described herein.

BRIEF DESCRIPTION OF THE DRAWINGS

FIG. 5 shows another example embodiment of a molding device comprising three molding stations (1, 2, 5) and one demolding station (3);

DETAILED DESCRIPTION OF THE INVENTION

Figure 1:
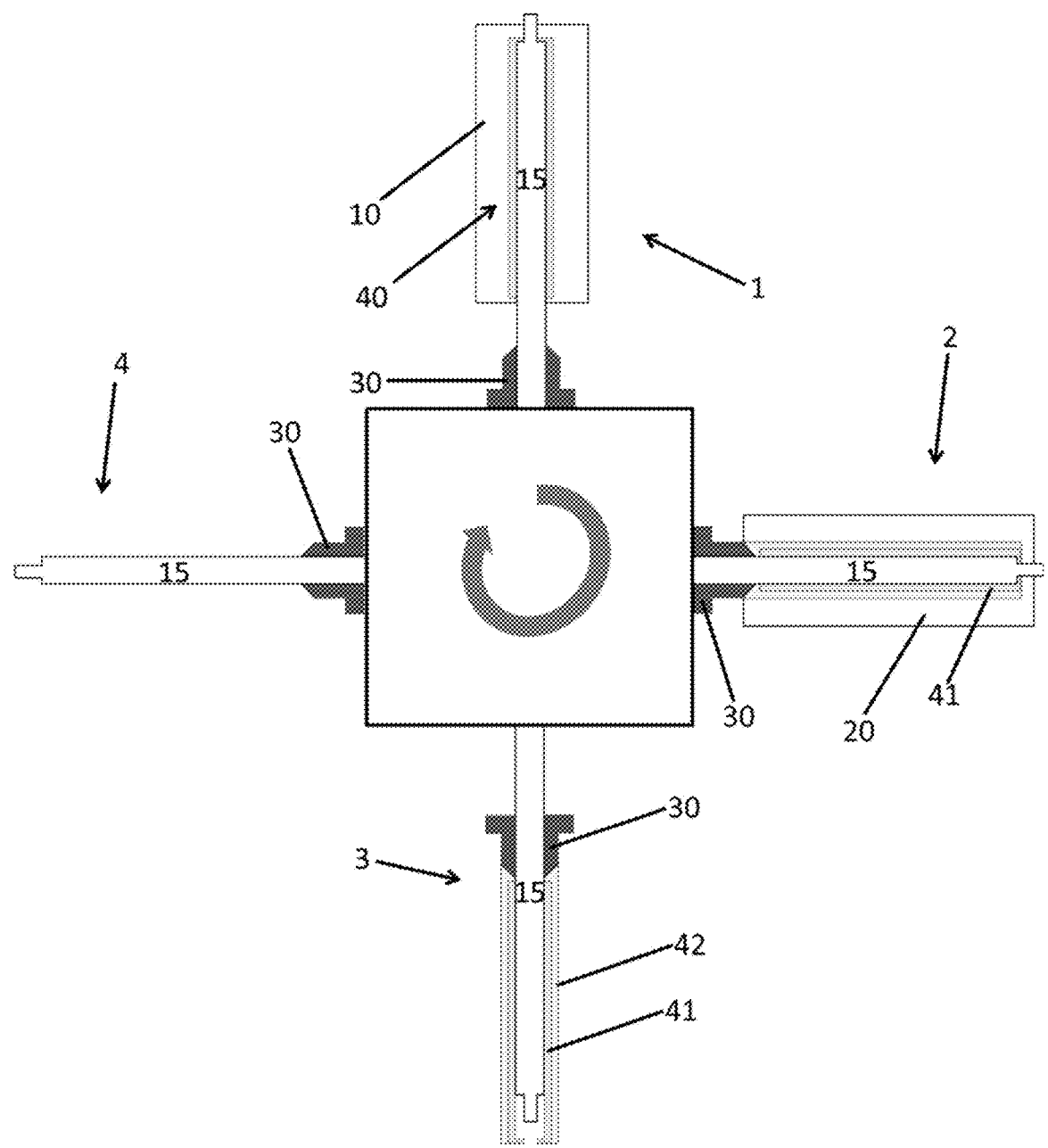
FIG. 1 shows an example embodiment of a molding device comprising two molding stations (1, 2) and one demolding station (3)

The following is a description of numerous embodiments of an injection molding device comprising at least one movable stripper and a method of producing hollow parts using said molding device. The description is to be construed as exemplary only and does not describe every possible embodiment since describing every possible embodiment would be impractical, if not impossible, and it will be understood that any feature, characteristic, structure, component, step or methodology described herein can be deleted, combined with or substituted for, in whole or in part, any other feature, characteristic, structure, component, product step or methodology described herein.

In accordance with one aspect of the disclosure, there is provided a molding device for manufacturing of at least one plastic object by injection molding, wherein the plastic object is a hollow part. As understood herein a "hollow part" refers to any plastic object which is manufactured by injection molding and comprises a hollow. Said hollow is formed by injecting the plastic object onto a core which is located at least partially inside of the mold cavities. As a skilled artisan would readily recognize, the term "core" in the present context is an element used in casting and molding machines and processes to produce internal cavities in parts being manufactured. In other words, a core can be viewed as an insert or a protrusion into the plastic part being manufactured to form a cavity/void therein upon solidification of the plastic material. During a molding process, one end of the cores can be covered at least partially by the injected hollow part being made while the other end may remain free of the injected hollow part. The end of the core which is located at least partially inside of the mold cavities and which is covered with the hollow part after the injection of the plastic took place is termed a first end of the core. In addition, a part of the first end of the core may reach through the mold cavities, thereby forming a through-hole in the plastic hollow part to be formed by injection molding.

The molding device comprises at least two different molding stations. At each molding station another part and/or layer of the hollow part is injected. The different parts and/or layers which are injected at the different molding stations may be for example complete layers, partial layers, localized plastic parts and/or mixtures thereof. The parts of the hollow part which are already injected are located onto the core and can be transferred from one injection molding station to another injection molding station by transferring the core. For example, the different injection molding stations may be arranged adjacent to each other in a linear manufacturing line and the core is transferred from one end of the manufacturing line to the other end of the manufacturing line. In addition or alternatively, the different molding stations may be arranged along a circular manufacturing line. For example, different stations may be arranged along a circle or a rectangle and the core can be arranged from one station to another station by rotation. Depending on the number of molding stations which are arranged around the circle or rectangle the degree of rotation is chosen accordingly, e.g. a rotation of 90° is used if four stations are arranged. In addition, more than one hollow part can be injected in parallel at each molding station, if more than one mold cavities are arranged at each molding station. For sake of readability only one mold cavity is described for each station, although the invention is not limited to that embodiment.

As already described the hollow part which can be injected using a molding device as described herein is injected onto a core. That means after passing all injection molding stations needed to inject all parts of the hollow part the hollow part has to be removed from the core. Therefore at least one stripper is located at the second end of the core which is not covered by the hollow part in order to remove the hollow part from the core. During said removing action the at least one stripper is moved along the core in the direction of the first end of the core which is covered at least partially with the hollow part. According to the present description said at least one stripper is not only a stripper for removing the hollow part, but also forms a part of at least one of the mold cavities during the injection molding process. That means the at least one stripper is located onto the surface of the core in more than one position and can be moved onto the core from one position into the other position. For example, the at least one stripper can be located onto the core in three different positions with three different distances from the first end of the core which is located at least partially inside of the mold cavity. Said at least one stripper may be for example a complete or a partial ring. Any heat resistant material which is resistant to hot melted plastic material may be used to form the stripper as disclosed herein. In particular, steel, such as working steel or stainless steel can be used.

In addition or alternatively, more than one stripper can be arranged onto the core. For example two or more strippers are arranged onto the core which may be structures which only partially cover the core, such as partial rings, slides, pushers etc. The two or more strippers may be located at opposite sides of the core. If two or more strippers are used in the molding device as described herein, all strippers are movable and comprise the functionalities as disclosed. The strippers may be of identical or different size and/or form. In addition, the strippers may be located at identical or different positions onto the core relative to each other, if they are in their functional positions.

In particular, the stripper(s) can be arranged onto the core in at least three different positions. In a first position, which is a passive position, the stripper(s) is arranged near to the second end of the core which is not covered by the mold cavities. In particular, the stripper(s) is located outside the mold cavities and does not contact the mold. That means the distance from the first end of the core to the position of the stripper(s), in particular to a first end of the stripper(s), is at least larger than the space of the mold cavity and the size of the mold. If more than one stripper is arranged in the passive position, the location of the passive position relative to the core may be identical or different to each other. As the passive position must not meet any functional requirement, the position is determined by the geometric requirements of the first mold and/or the first molding station.

In a second position, which is a molding position, the stripper(s) form a part of the mold. That means the stripper(s) are arranged onto the core in such that it/they limit(s) the mold cavity. Thus, the molding position is termed "molding position" due to the functional requirement the stripper(s) has/have to meet. That means the stripper(s), in particular the first end(s) of the stripper(s) which form part of the mold are arranged with a distance from the first end of the core which is smaller than the distance of the passive position of the stripper(s).

Due to the fact that the first end(s) of the stripper(s) form part of the mold, the form of said end(s) is adapted accordingly. Any suitable form may be used for the first end(s) of the stripper(s). For example, inclined surfaces, recesses, projections and/or combinations thereof may be present at the first end(s) of the stripper(s). That means, due to the stripper(s) which is/are part(s) of the mold, complex parts of the hollow part, e.g. undercuts, can be realized easily during the injection molding process. If more than one stripper is used, the strippers may have different first ends in order to form different parts of the hollow part. In addition or alternatively, the strippers may be located in their molding position at different positions onto the core in order to inject different parts of the hollow part. If more than one stripper is used and all strippers have identical ends and are arranged at an identical molding position a plurality of identical form elements can be injected at the hollow part. The stripper(s) can be used in their molding position for one or more molding steps of one molding series.

In a third position, a demolding position, the stripper(s) is/are arranged onto the core in such that the stripper(s) remove/strip the hollow part from the core. The demolding position is the position which is nearest to the first end of the core. That means the distance from the first end of the core to the first end of the stripper(s) in the demolding position is smaller than the size of the hollow part. In particular, the distance is smaller in such that the hollow part is stripped from the core. For example, the distance from the first end of the core to the first end of the stripper(s) in the stripping position is smaller than 50%, preferable smaller than 60%, more preferred smaller than 70% of the length of the second mold cavity defining the size of the hollow part. If more than one stripper is used the demolding position of the two or more strippers relative to the core may be identical or different. In particular, if the injected hollow part is asymmetric the demolding positions of the strippers may be adapted to the dimension of the hollow part.

Each of the mold cavities of the molding device into which plastic material can be injected to form the plastic hollow part as described herein may be formed by three or more parts. For example, the mold cavity may be formed by a first mold half and a second mold half. "A mold half" as used herein shall mean any part which forms a limiting wall or a part thereof of the mold cavity. In addition, the mold cavity is also limited by the core which is located at least partially in the mold cavity so that the hollow part can be injected onto the first end of the core. For example, a first and a second mold half may be a half of a mold forming the mold cavity and each of the mold halves or only one of the mold halves may comprise a space for the core. The plastic material will be injected into the mold cavity via injection nozzles. Hot runner and/or cold runner injection nozzles may be used. Thus, the molding device further comprises at least one injection nozzle, in particular the molding device comprises at least one injection nozzle per molding station.

The molding device comprises a molding station, wherein the stripper(s) form(s) part of the mold cavity. In addition, the molding device comprises at least one molding station, wherein the stripper(s) do(es) not form part of the mold cavity. The molding station which uses the stripper(s) as part of the mold cavity may be in particular the last molding station before the demolding. In particular, the part of the hollow part which comprises the complementary form of the stripper(s) is not overmolded in other molding stations so that the stripper(s) perfectly match to the hollow part during demolding.

According to another aspect a method for manufacturing a plastic hollow part by injection molding is provided. Said method comprises the step of injecting a first plastic material onto a core which is located partially in a first mold cavity in order to form a first part of a hollow part. At the surface of the core a stripper is located outside the first mold cavity in a passive position. Then the core is transferred together with the first part of the hollow part to a second mold and the stripper is moved from the passive position to a molding position wherein the stripper forms a part of the second mold in its molding position. Then a second plastic material is injected into the second mold thereby forming a second part of the hollow part which is injected onto the first part of the hollow part. After opening the second mold the hollow part is stripped from the core by moving the stripper into its demolding position which is located at the core at a position which was covered by the second mold before. That means the stripper is used as part of the second mold and a part of the second mold comprises the function of a stripper for re-movement of the hollow part from the core during the demolding process. During the first molding step the stripper is not needed functionally so that it rests onto the core in a passive position. In addition or alternatively, a method for manufacturing a hollow part by injection molding is provided, wherein the method uses a molding device as disclosed herein. While the description describes the molding steps one after the other, it is apparent that a molding step can be/will be performed at each station simultaneously, wherein each molding station performs its respective operation.

According the another aspect a plastic hollow part is provided, wherein the plastic hollow part is manufactured with a molding device as disclosed herein and/or with a method as disclosed herein. Said plastic hollow part may be a hollow part of any form and function. For example a bottle, a box, a catch, a case, a housing or a combination thereof may be injected as hollow part. In particular, a housing for a motor and/or a driving part of an electric toothbrush, such as a handle of an electric toothbrush may be injected as hollow part using the method and/or the molding device as disclosed herein. If the method and/or molding device as disclosed herein are used complex forms of the hollow part can be realized easily. For example, the plastic hollow part as disclosed herein may comprise one or more undercut(s) formed by the stripper(s) which are used as part of the mold.

In the following, a detailed description of several example embodiments will be given. It is noted that all features described in the present disclosure, whether they are disclosed in the previous description of more general embodiments or in the following description of example embodiments, even though they may be described in the context of a particular embodiment, are of course meant to be disclosed as individual features that can be combined with all other disclosed features as long as this would not contradict the gist and scope of the present disclosure. In particular, all features disclosed for either one of the molding device, the stripper(s), the core, the mold halves, the method for manufacturing of a hollow part or the hollow part itself may also be applied to the other one, if applicable.

FIG. 1 shows an example embodiment of a molding device comprising two molding stations 1,2, one demolding station 3 and one station 4 which is not used. As a first station 1 a first molding station is shown after plastic material was injected onto a core 15 in a first mold 10 in order to form a plastic hollow part 40. A movable stripper 30 which is a ring is arranged onto the core 15 in a passive position outside the mold 10. As a second station 2 a second molding station is shown after plastic material was injected onto the hollow part 41 formed in station 1 in a second mold 20. The movable stripper 30 is arranged onto the core 15 in its molding position, as part of the mold 20. As a third station 3 a demolding or stripping station is shown during the stripping process, whereby the hollow part 40 comprising a first part 41 injected at the first molding station 1 and a second part 42 injected at the second molding station 2 is removed from the core 15. The movable stripper 30 is arranged onto the core 15 in its demolding position. At a fourth position 4 the core 15 is shown alone and the movable stripper 30 rests in its passive position again. The core 15 can be transferred from one station to the next station by rotation of 90°. A more detailed view of the stations is shown in FIGS. 2 to 4.

Figure 2A:
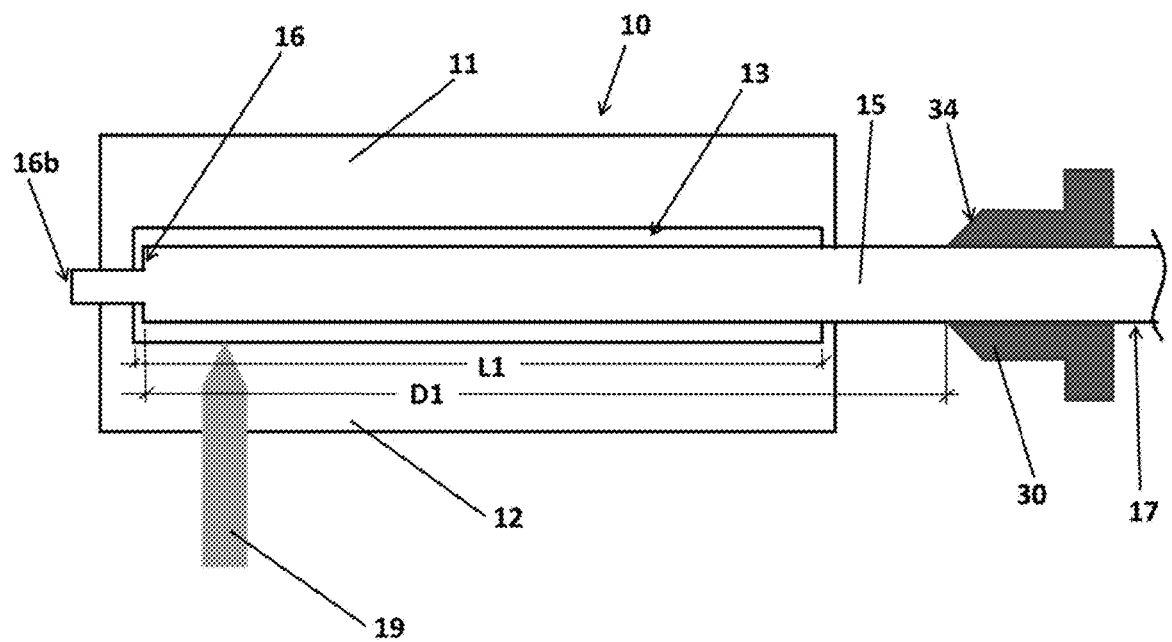
FIGS. 2A and 2B show an enlarged view of the first molding station 1 of FIG. 1 before (A) and after (B) plastic material was injected.

FIG. 2A shows an enlarged view of the first molding station 1 before plastic material was injected. All features disclosed in FIG. 1, whether described individually or in combination are also applicable to the embodiment shown in FIG. 2A. Features that are in common with the molding device shown in FIG. 1 are designated with the same reference numerals and are not described in detail again. A first mold half 11 and a second mold half 12 are arranged to form a first mold 10 comprising a first mold cavity 13. An injection nozzle 19 passes through the second mold half 12 into the first mold cavity 13. A core 15 is arranged with its first end 16 at least partially inside the first mold cavity 13. A part of the first end 16, namely 16b, is arranged outside the first mold cavity 13 so that the core 15 ranges through the first and second mold halves 11, 12. At the surface 17 of the core 15 a movable stripper 30 in form of a ring is arranged at the core 15 outside the mold cavity 13. The position of the stripper 30 onto the core 15 is changeable. In a passive position as shown in FIG. 2 the stripper 30 is arranged outside the mold 10. That means a distance D1 covering the length from the part of the first end 16 which is located inside the first mold cavity 13 to a first end 34 of the stripper 30 is at least larger than the mold cavity 13 having a length L1. A suitable distance D1 for a molding station 1 into which a handle of an electric toothbrush can be injected is in the range of 170 to 220 mm, preferably in the range of 190 mm to 200 mm.

Figure 2B:
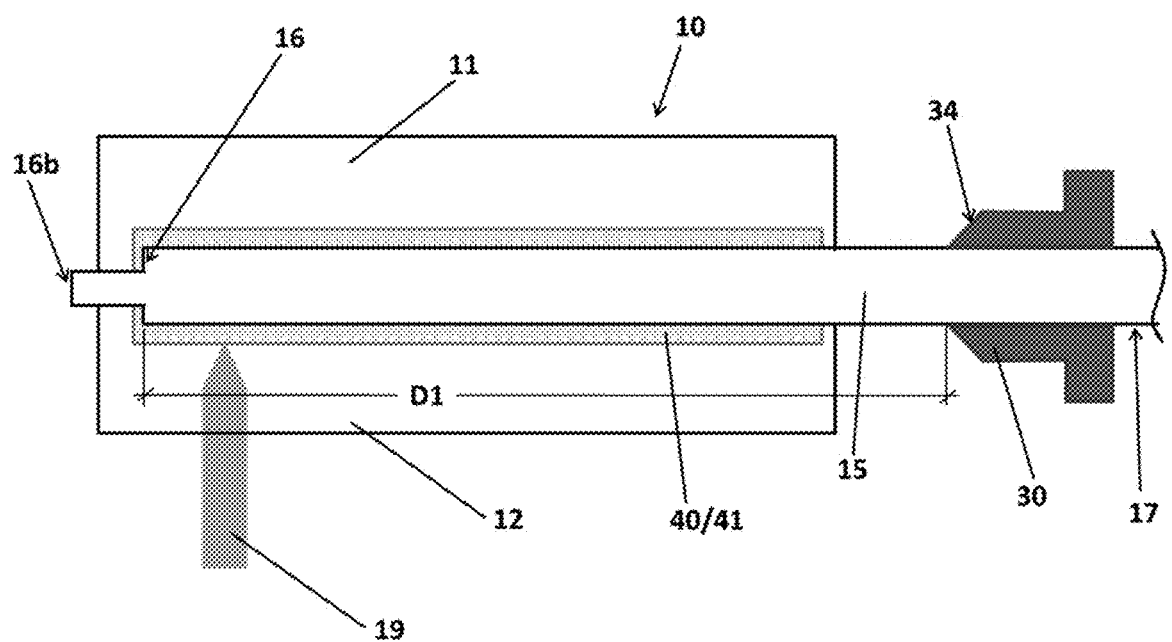

FIG. 2B shows an enlarged view of the first molding station 1 after plastic material was injected. All features disclosed in FIG. 1 and FIG. 2A, whether described individually or in combination are also applicable to the embodiment shown in FIG. 2B. Features that are in common with features shown before are designated with the same reference numerals and are not described in detail again. Through the injection nozzle 19 hot melted plastic material was injected into the first mold cavity 13 (FIG. 2A). Thus, a first part 41 of a hollow part 40 was formed in the mold cavity onto the core 15. The stripper 30 rests in its passive position outside the mold 10.

Figure 3A:
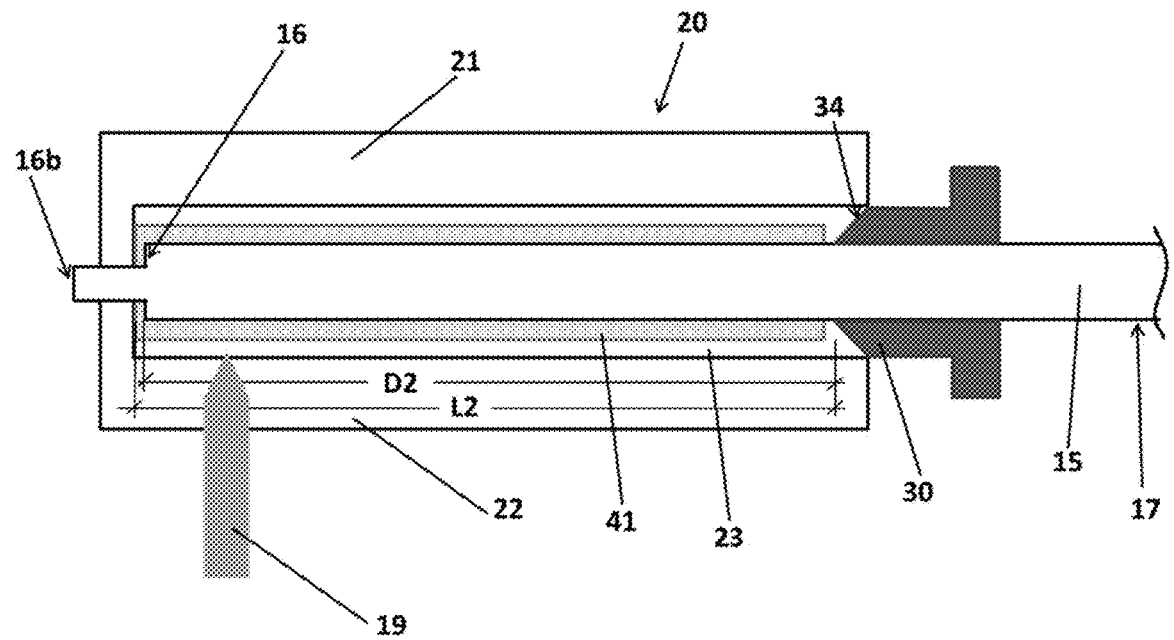
FIGS. 3A and 3B show an enlarged view of the second molding station 2 of FIG. 1 before (A) and after (B) plastic material was injected.

FIG. 3A shows an enlarged view of the second molding station 2 before plastic material was injected. All features disclosed in FIGS. 1 and 2, whether described individually or in combination are also applicable to the embodiment shown in FIG. 3. Features that are in common with the features shown before are designated with the same reference numerals and are not described in detail again. A first mold half 21 and a second mold half 22 are arranged to form a second mold 20 comprising a second mold cavity 23 having a length L2. An injection nozzle 19 passes through the second mold half 22 into the second mold cavity 23. A core 15 carrying the first part 41 of the hollow part 40 is arranged with its first end 16 inside the second mold cavity 23. A part of the first end 16, namely 16b, is arranged outside the second mold cavity 23 so that the core 15 ranges through the first and second mold halves 21, 22. The movable stripper ring 30 is arranged at the surfaces 17 of the core 15 in its molding position. In the molding position as shown in FIG. 3 the stripper 30 forms a part of the mold 20, thereby limiting a part of the mold cavity 23. That means a distance D2 from the first end 16 of the core 15 ending at the first end 34 of the stripper 30 is smaller than a distance D1 shown in FIG. 2. A suitable distance D2 for a molding station 2 into which a handle of an electric toothbrush can be injected is in the range of 140 mm to 180 mm, preferably in the range of 150 mm to 170 mm. As shown in FIG. 3A the first end 34 of the stripper 30 is inclined.

Figure 3B:
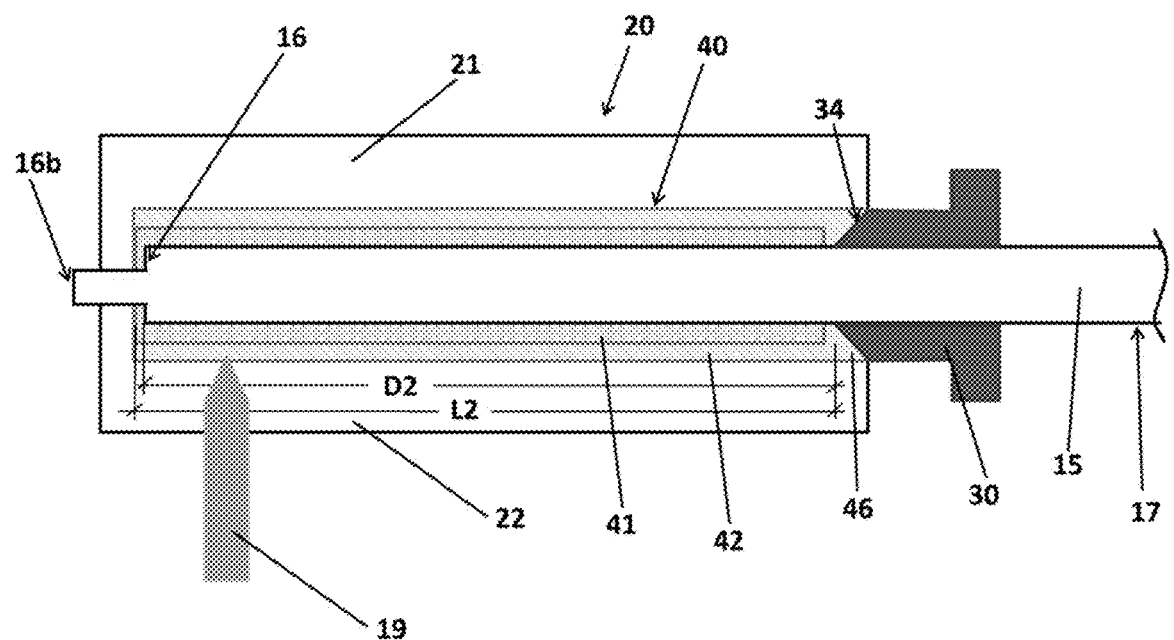

FIG. 3B shows an enlarged view of the second molding station 2 after plastic material was injected. All features disclosed in FIGS. 1, 2 and 3A, whether described individually or in combination are also applicable to the embodiment shown in FIG. 3B. Features that are in common with features shown before are designated with the same reference numerals and are not described in detail again. Through the injection nozzle 19 hot melted plastic material was injected into the second mold cavity 23 thereby forming the second part 42 of the hollow part 40. Thus, the hollow part 40 now comprises a double layer of plastic material 41, 42. In its molding position the stripper 30 limits the mold cavity 23, i.e. is part of the mold 20. Due to the inclined first end 34 of the stripper 30 an undercut 46 was formed at the second part 42 of the hollow part 40. As is shown in FIGS. 3A and 3B, when the stripper (30) is being arranged on the core (15) in a molding position at the second molding station (2), the second length (L2) of the second mold cavity (23) extends from the first end (34) of the stripper (30) towards the first end (16) of the core (15).

Figure 4A:
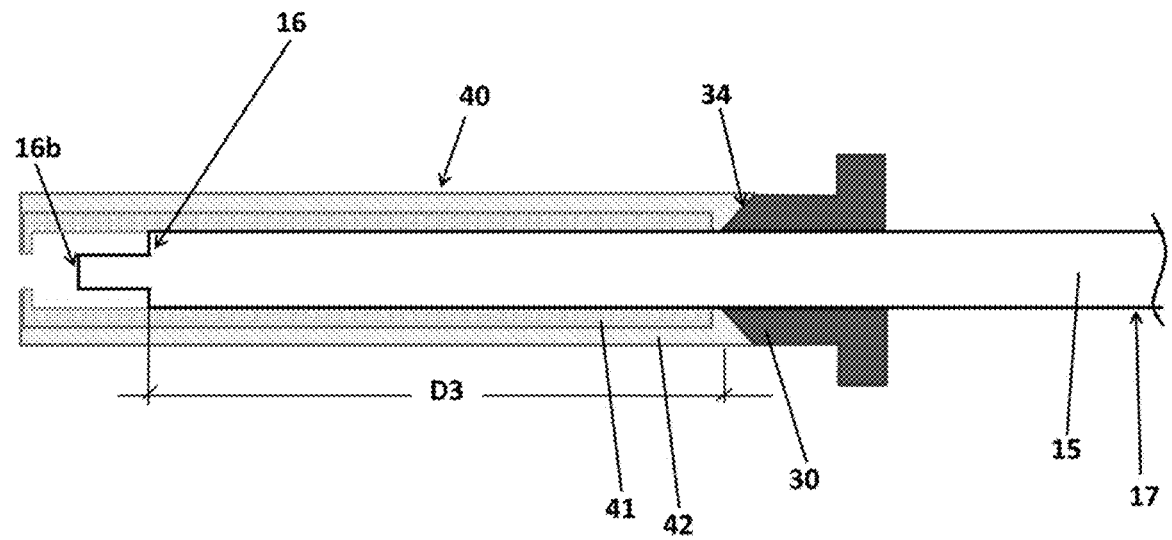
FIGS. 4A, 4B and 4C show an enlarged view of the demolding station 3 of FIG. 1 during the stripping process.

FIG. 4A shows an enlarged view of the demolding station 3 during the hollow part 40 is striped off. All features disclosed in FIGS. 1 to 3, whether described individually or in combination are also applicable to the embodiment shown in FIG. 4A. Features that are in common with the features shown before are designated with the same reference numerals and are not described in detail again. After the second mold 20 was opened the core 15 together with the double layered (41, 42) hollow part 40 was removed from the second molding station 2 (FIG. 3) by rotation of 90°. The movable stripper 30 is arranged at the core 15 in its demolding position. That means the movable stripper 30 was moved from the molding position shown in FIG. 3 along the core 15 in the direction of the first end 16 of the core 15 until the demolding position as shown in FIG. 4A has been reached. During the movement of the stripper 30 into the demolding position the stripper 30 strips off the hollow part 40 from the core 15. That means a distance D3 ranging from the first end 16 of the core 15 to the first end 34 of the stripper 30 is smaller than the length L2 of the second mold cavity 23 as shown in FIG. 3. A suitable distance D3 for a demolding station 3 at which a handle of an electric toothbrush can be stripped off is about 50%, preferably 60%, more preferred 70% smaller than the length L2 of the second mold cavity 23 shown in FIG. 3.

Figure 4B:
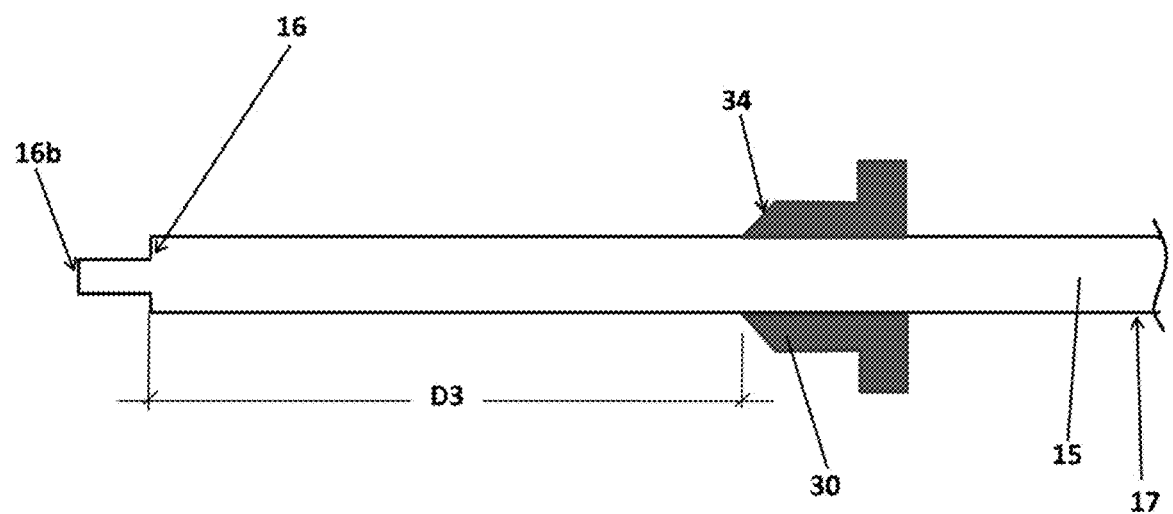

FIG. 4B shows an enlarged view of the demolding station 3 after the hollow part 40 was stripped off from the core 15. The stripper 30 rests in its demolding position. All features disclosed in FIGS. 1 to 4A, whether described individually or in combination are also applicable to the embodiment shown in FIG. 4B. Features that are in common with the features shown before are designated with the same reference numerals and are not described in detail again.

Figure 4C:
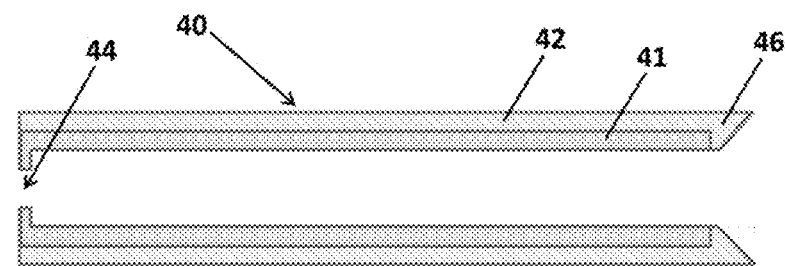

FIG. 4C shows the double layered hollow part 40 comprising a first part 41 and a second part 42 after being completely separated from the core 15. Due to the use des stripper 30 as part of the mold 20 a undercut 46 was formed (s. FIG. 3B) at one end of the hollow part 40. At the opposite end of the hollow part 40 a through-hole 44 was formed by the part 16b of the core 15 which reaches through the mold 20 (s. FIG. 3B). All features disclosed in FIGS. 1 to 4B, whether described individually or in combination are also applicable to the embodiment shown in FIG. 4C. Features that are in common with the features shown before are designated with the same reference numerals and are not described in detail again.

FIG. 5 shows another example embodiment of a molding device comprising three different molding stations 1, 2, 5 and one demolding station 3. In a first position a first molding station 1 is shown after plastic material was injected onto a core 15 in a first mold 10. A movable stripper 30 which comprises at least a first movable stripper 36 and a second movable stripper 37 is arranged onto the core 15 in a passive position outside the mold 10. In a second position a third molding station 5 is shown after plastic material was injected in a third mold 50 in order to form an intermediate part 45 of the hollow part 40. The intermediate part 45 was was injected onto the hollow part 41 which was formed at a first molding station 1. The movable strippers 36, 37 are arranged onto the core 15 in a passive position outside the mold 50. In a third position a second molding station 2 is shown after plastic material was injected onto the intermediate part 45 formed at the third molding station 5 in order to form a second part 42 of the hollow part 40 in a second mold 20. The movable strippers 36, 37 are arranged onto the core 15 in their molding position, as part of the mold 20. In a fourth position 3 a demolding station is shown during the stripping process, whereby the hollow part 40 comprising a first part 41 injected at the first molding station 1, an intermediate part 45 injected at the third molding station 5 and a second part 42 injected at the second molding station 2 is removed from the core 15. The movable strippers 36, 37 are arranged onto the core 15 in their demolding position. The core 15 can be transferred from one station to the next station by rotation of 90°.

Figure 6A:
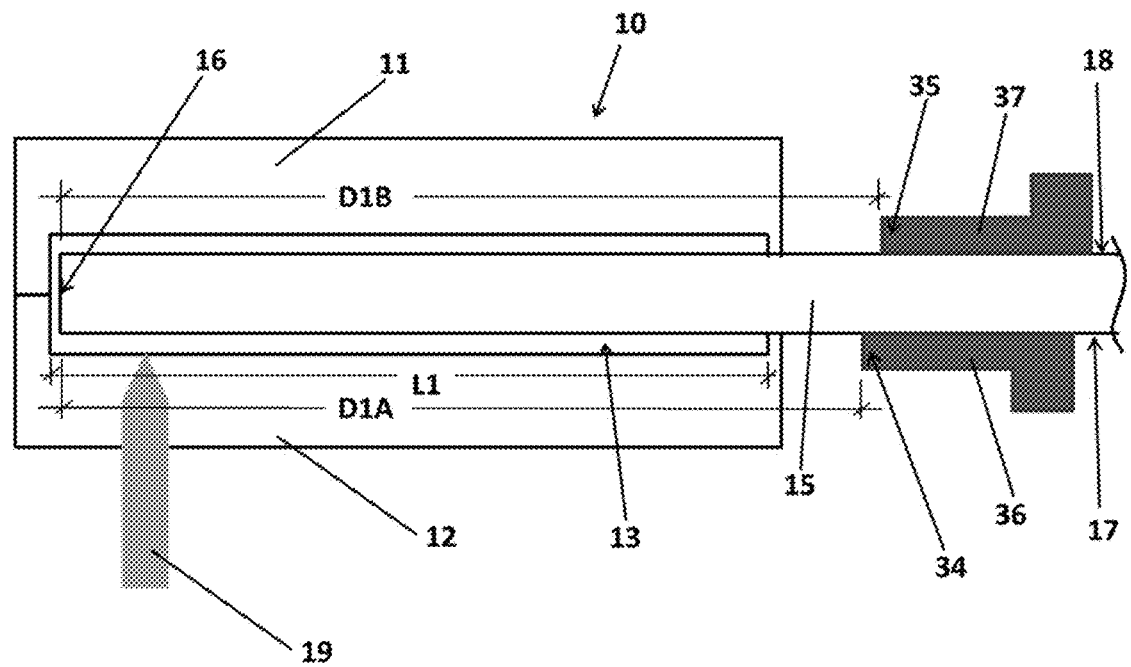
FIG. 6A shows an enlarged view of a second example embodiment of a first molding station 1 as shown in FIG. 1 before plastic material was injected, wherein a stripper (36, 37) consists of two equally formed parts arranged at different positions.

FIG. 6A shows an enlarged view of a second example embodiment of a first molding station 1 as shown in FIG. 5 before plastic material was injected, wherein a stripper (36, 37) consists of two equally formed parts which are arranged in two different positions. Features that are in common with the molding devices shown before are designated with the same reference numerals. A first mold half 11 and a second mold half 12 are arranged to form a first mold 10 comprising a first mold cavity 13 having a length L1. An injection nozzle 19 passes through the second mold half 12 into the first mold cavity 13. A core 15 is arranged with its first end 16 inside the first mold cavity 13. At opposite surfaces 17, 18 of the core 15 and at the end which is not located inside the mold cavity 13 movable strippers 36, 37 are arranged at the core 15. The position of the strippers 36, 37 onto the core 15 is changeable. In a passive position as shown in FIG. 6A the strippers 36, 37 are arranged outside the mold 10 and at different positions relative to each other. That means a distance D1A reaching from a first end 16 of the core 15 and ranging to a first end 34 of the first stripper 36 is at least larger than the mold cavity 13 having the length L1. In addition, a distance D1B reaching from a first end 16 of the core 15 and ranging to a first end 35 of the second stripper 37 is at least larger than the mold cavity 13 having the length L1 and is different to the distance D1A. A suitable distance D1A and/or D1B for a molding station 1 into which a handle of an electric toothbrush can be injected is in the range of 170 mm to 220 mm, preferably in the range of 190 mm to 200 mm.

Figure 6B:
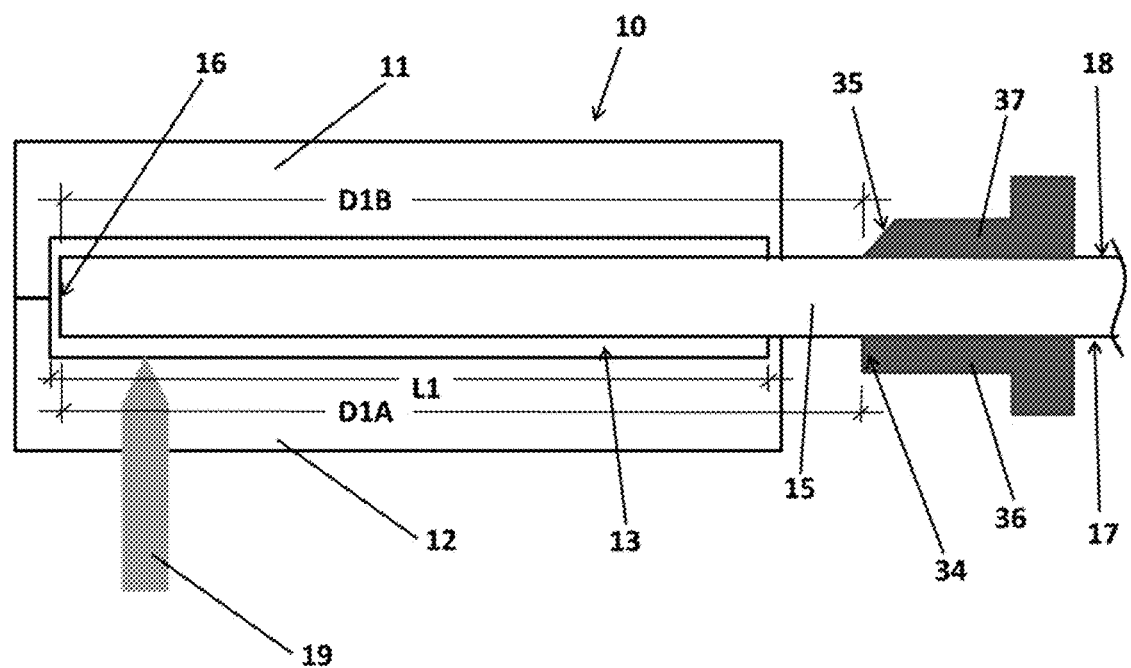
FIG. 6B shows an enlarged view of a third example embodiment of a first molding station 1 as shown in FIG. 1 before plastic material was injected, wherein a stripper (36, 37) consists of two different parts.

FIG. 6B shows an enlarged view of a third example embodiment of a first molding station 1 as shown in FIG. 5 before plastic material was injected, wherein a stripper (36, 37) consists of two parts with are differently formed. The different strippers 36, 37 are arranged at the same position at the core 15, but at opposite surfaces 17, 18. Features that are in common with the molding devices shown before are designated with the same reference numerals and are not described in detail again. A first mold half 11 and a second mold half 12 are arranged to form a first mold 10 comprising a first mold cavity 13 having the length L1. An injection nozzle 19 passes through the second mold half 12 into the first mold cavity 13. A core 15 is arranged with its first end 16 inside the first mold cavity 13. At opposite surfaces 17, 18 of the core 15 and at the end which is not located inside the mold cavity 13 movable strippers 36, 37 are arranged at the core 15. The position of the strippers 36, 37 onto the core 15 is changeable. In a passive position as shown in FIG. 6B the strippers 36, 37 are arranged outside the mold 10 and at identical positions relative to each other onto the core 15. That means a distance D1A from a first end 16 of the core 15 and ranging to a first end 34 of the first stripper 36 and a distance D1B from a first end 16 of the core 15 and ranging to a first end 35 of the second stripper 37 are identical. Distances D1A and D1B are at least larger than the mold cavity 13 having the length L1 of the mold 10. A suitable distance D1A/D1B for a molding station 1 into which a handle of an electric toothbrush can be injected is in the range of 170 mm to 220 mm, preferably in the range of 190 mm to 200 mm.

Figure 7A:
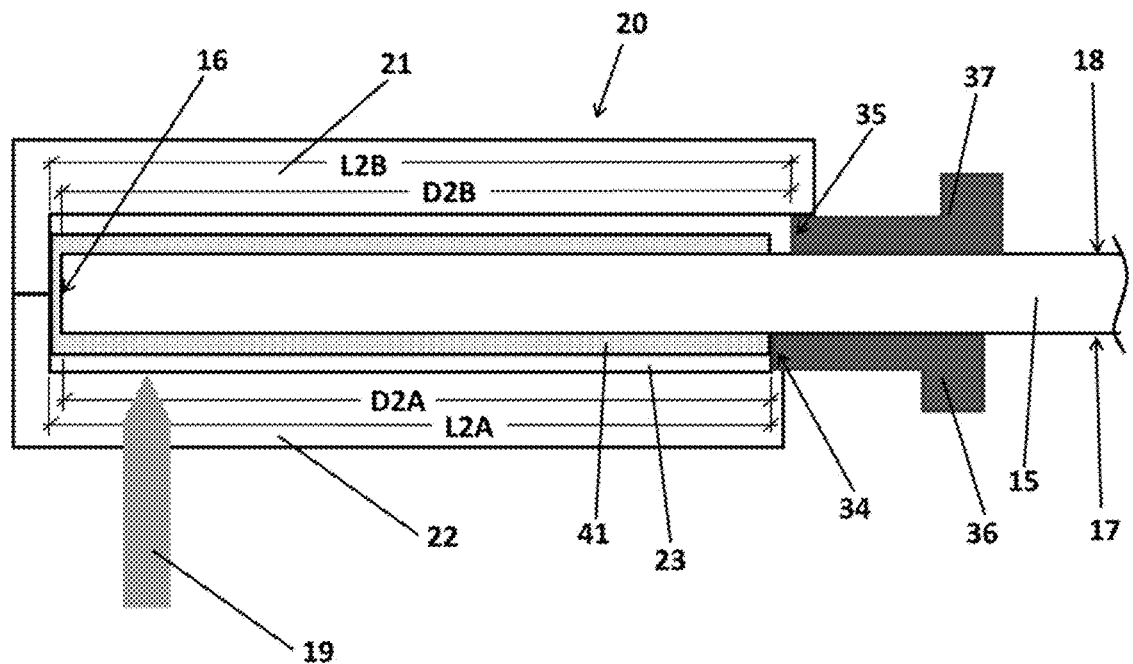
FIG. 7A shows an enlarged view of the second example embodiment of a second molding station 2 as shown in FIG. 1 before plastic material was injected, wherein a stripper (36, 37) consists of two equally formed parts arranged at different positions.

FIG. 7A shows an enlarged view of the second example embodiment of the second molding station 2 as shown in FIG. 5 before plastic material was injected. Movable strippers 36, 37 which show the same geometric form and dimension are arranged at different positions onto the core 15 and limit the mold cavity 23. Features that are in common with the features shown before are designated with the same reference numerals and are not described in detail again. A first mold half 21 and a second mold half 22 are arranged to form a second mold 20 comprising a second mold cavity 23. An injection nozzle 19 passes through the second mold half 22 into the second mold cavity 23. A core 15 carrying a first part 41 of the hollow part 40 is arranged with its first end 16 inside the second mold cavity 23. At opposite surfaces 17, 18 of the core 15 and at the end which is not located inside the mold cavity 23 the movable strippers 36, 37 are arranged at the core 15. The position of the strippers 36, 37 onto the core 15 is in their molding position. In the molding position as shown in FIG. 7A the strippers 36, 37 form part of the mold 20 and limit the mold cavity 23. Due to the fact that the strippers 36, 37 are arranged at different positions at the core 15 the mold cavity 23 is asymmetric having two different lengths L2A, L2B at the positions of the strippers 36, 37. That means a distance D2A from a first end 16 of the core 15 and ending at the first end 34 of the first stripper 36 is different to a distance D2B from a first end 16 of the core 15 and ending at the first end 35 of the first stripper 37. A suitable distance D2A/D2B for a molding station 2 into which a handle of an electric toothbrush can be injected is in the range of 140 mm to 180 mm, preferably in the range of 150 mm to 170 mm.

Figure 7B:
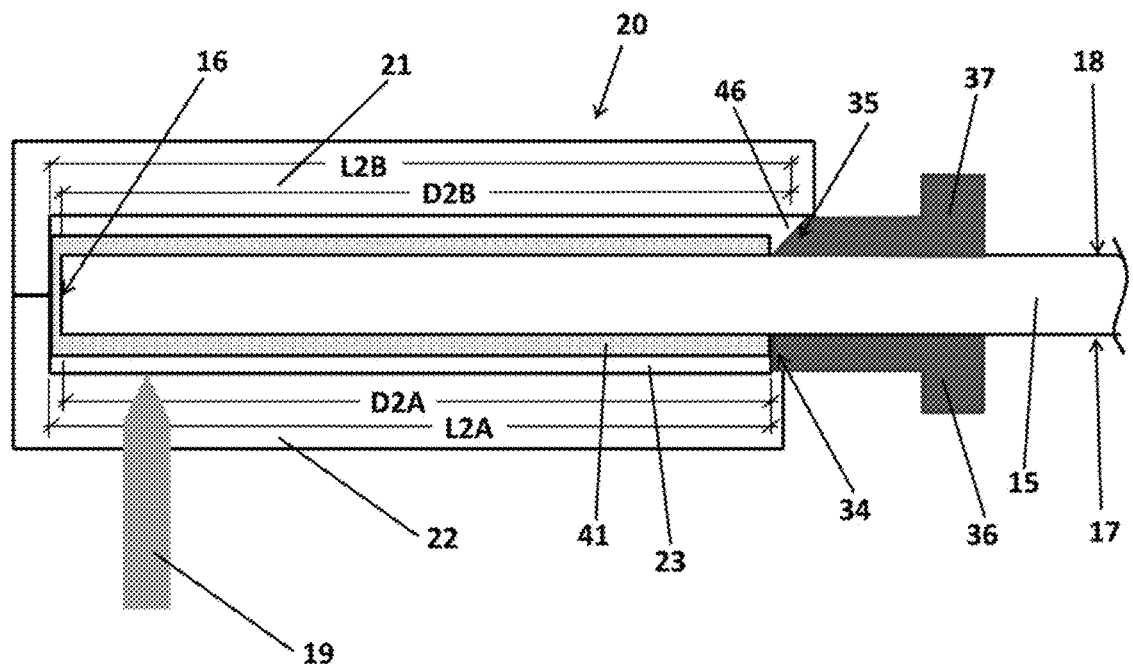
FIG. 7B shows an enlarged view of the third example embodiment of a second molding station 2 as shown in FIG. 1 before plastic material was injected, wherein a stripper (36, 37) consists of two different parts.

FIG. 7B shows an enlarged view of the third example embodiment of the second molding station 2 as shown in FIG. 5 before plastic material was injected. Features that are in common with the features shown before are designated with the same reference numerals and are not described in detail again. A first mold half 21 and a second mold half 22 are arranged to form a second mold 20 comprising a second mold cavity 23. An injection nozzle 19 passes through the second mold half 22 into the second mold cavity 23. A core 15 carrying a first part 41 of the hollow part 40 is arranged with its first end 16 inside the second mold cavity 23. At opposite surfaces 17, 18 of the core 15 and at the end which is not located inside the mold cavity 23 movable strippers 36, 37 which show different geometric forms are arranged at the core. The position of the strippers 36, 37 onto the core 15 is in their molding position. In the molding position as shown in FIG. 7B the strippers 36, 37 form part of the mold 20 thereby limiting the cavity 23. Due to the fact that the strippers 36, 37 are shaped differently the mold cavity 23 is asymmetric having two different lengths L2A, L2B at the positions of the strippers 36, 37. That means a distance D2A covering the second mold cavity 23 and ending at the first end 34 of the first stripper 36 is different to a distance D2B covering the second mold cavity 23 and ending at the first end 35 of the first stripper 37. Due to the inclined first end 35 of the stripper 37 an undercut 46 was formed at the second part 42 of the hollow part 40. A suitable distance D2A/D2B for a molding station 2 into which a handle of an electric toothbrush can be injected is in the range of 140 mm to 180 mm, preferably in the range of 150 mm to 170 mm.

Figure 8A:
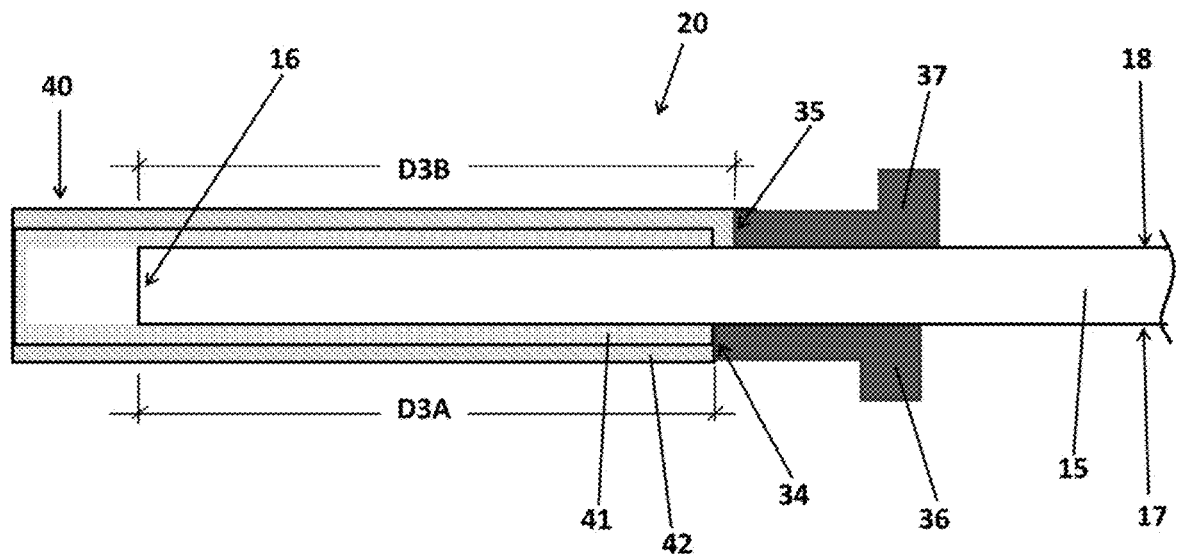
FIG. 8A shows an enlarged view of the second example embodiment of a demolding station 3 as shown in FIG. 1 before plastic material was injected, wherein a stripper (36, 37) consists of two equally formed parts arranged at different positions.

FIG. 8A shows an enlarged view of the second example embodiment of a demolding station 3 as shown in FIG. 5 during the hollow part 40 is striped off. Features that are in common with the features shown before are designated with the same reference numerals and are not described in detail again. After the second mold 20 was opened the core 15 together with the double layered (41,42) hollow part 40 was removed from the second molding station 2 by rotation of 90°. The movable strippers 36, 37 are arranged at the core 15 in their demolding position. That means the movable strippers 36, 37 were moved from the molding position shown in FIG. 7A along the core 15 in the direction of the first end 16 of the core 15 until the demolding position as shown in FIG. 8A has been reached. During the movement of the strippers 36, 37 into the demolding position the strippers 36, 37 strip off the hollow part 40 from the core 15. That means a distance D3A ranging from the first end 16 of the core 15 to the first end 34 of the first stripper 36 and/or distance D3B ranging from the first end 16 of the core 15 to the first end 35 of the second stripper 37 is smaller than the distance D2A/D2B as shown in FIG. 7A. The demolding position of the first and second stripper 36, 37 onto the core 15 is different relative to each other as the size of the hollow part 40 is also different at the positions of the strippers 36, 37. A suitable distances D3A, D3B for a demolding station 3 at which a handle of an electric toothbrush can be stripped off is about 50%, preferably 60%, more preferred 70% smaller than the length L2A/L2B of the mold cavity 23 as shown in FIG. 7A.

Figure 8B:
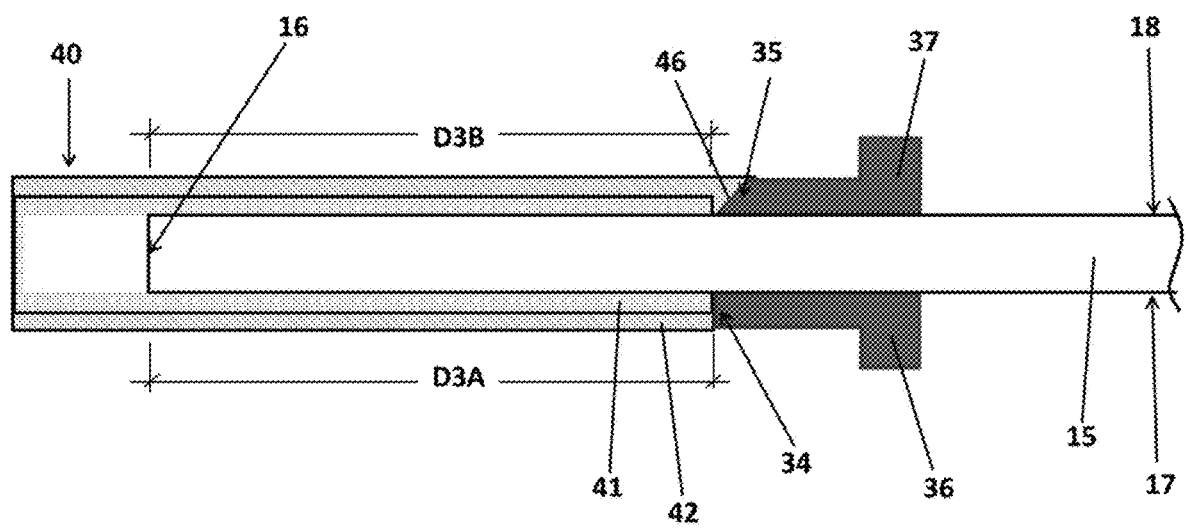
FIG. 8B shows an enlarged view of the third example embodiment of a demolding station 3 as shown in FIG. 1 before plastic material was injected, wherein a stripper (36, 37) consists of two different parts.

FIG. 8B shows an enlarged view of the third example embodiment of a demolding station 3 as shown in FIG. 5 during the hollow part 40 is striped off. Features that are in common with the features shown before are designated with the same reference numerals and are not described in detail again. After the second mold 20 was opened the core 15 together with the double layered (41, 42) hollow part 40 was removed from the second molding station 2 by rotation of the core 15 by 90°. The movable strippers 36, 37 are arranged at the core 15 in their demolding position. That means the movable strippers 36, 37 were moved from the molding position shown in FIG. 7B along the core 15 in the direction of the first end 16 of the core 15 until the demolding position as shown herein has been reached. During the movement of the strippers 36, 37 into the demolding position the strippers 36, 37 strip off the hollow part 40 from the core 15. That means a distance D3A ranging from the first end 16 of the core 15 to the first end 34 of the first stripper 36 and/or distance D3B ranging from the first end 16 of the core 15 to the first end 35 of the second stripper 37 is smaller than the distance D2A/D2B shown in FIG. 7B. As shown herein the demolding position of the first and second stripper 36, 37 onto the core 15 is identical relative to each other, but the strippers 36, 37 are differently shaped. Due to the inclined first end 35 of the stripper 37 an undercut 46 was formed at the second part 42 of the hollow part 40. A suitable distance D3A, D3B for a demolding station 3 at which a handle of an electric toothbrush can be stripped off is about 50% smaller, preferably 60% smaller, more preferred 70% smaller than the length L2A, L2B of the second mold cavity 23 as shown in FIG. 7B.

As is shown in FIGS. 2A-4 and 5-8B, during manufacturing, the plastic hollow part being manufactured is disposed, in its entirety and along the longitudinal axis, in front of the first end of the stripper.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What we claim is:

1. A molding device for manufacturing at least a plastic hollow part (40) by injection molding comprising
at least a first molding station (1) comprising at least a first mold (10) comprising a first mold half (11) and a second mold half (12) forming a first mold cavity (13) for molding a first part (41) of a hollow part (40), the first mold cavity (13) having a first length (L1);
at least a second molding station (2) comprising at least a second mold (20) comprising a first mold half (21) and a second mold half (22) forming a second mold cavity (23) for molding a second part (42) of the hollow part (40), the second mold cavity (23) having a second length (L2);
at least a demolding station (3) for demolding the plastic hollow part (40);
wherein a core (15) is transferable from the first molding station (1) to the second molding station (2) and/or to the demolding station (3), so that the core is locatable at least partially inside the first and second mold cavities (13, 23) thereby forming a part of the first and second mold cavities (13, 23), the core having a longitudinal axis and a first end (16), wherein the first length (L1) and the second length (L2) are parallel to the longitudinal axis;
wherein at least one stripper (30) is slidingly arranged on the core around an outer surface (17) of the core (15) for a sliding movement along the longitudinal axis whereby an inner surface of the stripper contacts the outer surface of the core, the stripper having a first end (34) and a second end spaced from the first end along the longitudinal axis so that the first end of the stripper (34) is disposed between the first end (16) of the core (15) and the second end of the stripper, the first end (34) of the stripper being structured and configured to face, in a direction parallel to the longitudinal axis, the plastic hollow part in its entirety;
wherein the stripper (30) is arranged on the core (15) in a passive position at the first molding station (1), wherein a first distance (D1) is formed between the first end of the core and the first end of the stripper, wherein at least a part of the first end (16) of the core (15) is located inside the first mold cavity (13) and the stripper (30) is located outside the first mold cavity (13);
wherein the stripper (30) is arranged on the core (15) in a molding position at the second molding station (2) so that the second length (L2) of the second mold cavity (23) extends from the first end (34) of the stripper (30) towards the first end (16) of the core (15), wherein a second distance (D2) is formed between the first end (16) of the core (15) and the first end (34) of the stripper (30), wherein at least a part of the first end (16) of the core (15) is located inside the second mold cavity (23) and the first end (34) of the stripper (30), together with the first mold half (21) and the second mold half (22) of the second mold (20), form the second mold cavity (23);
wherein the stripper (30) is arranged on the core (15) in a demolding position at the demolding station (3), wherein a third distance (D3) is formed between the first end (16) of the core (15) and the first end (34) of the stripper (30) when the core (15) is positioned outside of the first and second mold cavities (13, 23);
wherein the stripper (30) is structured and configured to slidingly move, along and in contact with the core (15), between the passive position, the molding position, and the demolding position; and
wherein, the first distance (D1), the second distance (D2), and the third distance (D3) are parallel to the longitudinal axis and wherein the first distance (D1) is larger than the second distance (D2) and the second distance (D2) is larger than the third distance (D3).

2. The molding device according to claim 1, wherein the first distance (D1) is larger than the first length (L1) of the first mold cavity (13).

3. The molding device according to claim 1, wherein the demolding position of the stripper (30) on the core (15) is located where at least a part of the hollow part (40) was located on the core (15) at the first and second molding stations (1,2).

4. The molding device according to claim 1, wherein the third distance (D3) is smaller than the second length (L2) of the second mold cavity (23).

5. The molding device according to claim 1, wherein the core (15) is transferable from the first molding station (1) to at least one of the second molding station (2) and the demolding station (3) by being rotated 90°.

6. The molding device according to claim 1, wherein the molding device comprises at least a third molding station (5) including at least a third mold (50) comprising a first mold half (51) and a second mold half (52) forming a third mold cavity (53) for molding a third part (43) of the hollow part (40), wherein the core (15) that is transferable from at least one of the first molding station (1) and the second molding station (2) to the third molding station (5) is locatable at least partially inside the third mold cavity (53) thereby forming a part of the third mold cavity (53), and wherein the stripper (30) is located outside the third mold cavity (53).

7. The molding device according to claim 1, wherein the first end (16) of the core (15) comprises a protrusion (16b) that reaches through at least one of the first mold (10), the second mold (20), and the third mold (50) to form a through-hole in the hollow part (40).

8. The molding device according to claim 1, wherein the stripper (30) is a ring.

9. The molding device according to claim 1, wherein the stripper (30) is arranged on the core (15) such that no portion of the plastic hollow part being manufactured is disposed between the outer surface of the core and the inner surface of the stripper.

10. The molding device according to claim 8, wherein the ring is a single-piece element.

11. The molding device according to claim 8, wherein the stripper comprises at least two parts.

12. The molding device according to claim 11, wherein the stripper is formed by the at least two parts arranged on the core's opposite surfaces.

13. The molding device according to claim 11, wherein the at least two parts comprise a first stripper part and a second stripper part and wherein at least one of the molding position and the demolding position of the first stripper part (36) relative to the core (15) is different from at least one of the molding position and the demolding position of the second stripper (37) relative to the core (15).

14. A method of manufacturing a plastic hollow part (40) by injection molding comprising
injecting a first plastic material into a first mold cavity (13) onto a core (15) having a longitudinal axis and a first end in order to form a first part (41) of a hollow part (40) at a first molding station (1);
transferring the core (15) together with the first part (41) of the hollow part (40) to a second mold (20) comprising a first mold half (21) and a second mold half (22) and injecting a second plastic material into a second mold cavity (23) onto the first part (41) of the hollow part (40) in order to form a second part (42) of the hollow part (40) at a second molding station (2);
transferring the core (15) together with the hollow part (40) to a demolding station (3) and removing the hollow part (40) from the core (15);
wherein the hollow part (40) is removed from the core (15) using a stripper (30) arranged on the core (15) for a slidable movement along the longitudinal axis wherein an inner surface of the stripper contacts and slides along an outer surface of the core, wherein the stripper has a first end and a second end spaced from the first end along the longitudinal axis so that the first end (34) of the stripper (30) is disposed between the first end (16) of the core (15) and the second end of the stripper (30), wherein the plastic hollow part being manufactured is disposed, in its entirety and along the longitudinal axis, in front of the first end (34) of the stripper (30), and wherein the stripper (30) is located outside the first mold cavity (13) at the first molding station (1) and wherein the first end of the stripper (30) forms the second mold cavity (23) together with the first mold half (21) and the second mold half (22) of the second mold (20).

15. The method according to claim 14, wherein the stripper is arranged on the core (15) adjacent to at least one of a first mold half (21) and a second mold half (22) at the second molding station (2) thereby limiting the second mold cavity (23).

16. The method according to claim 14, wherein the stripper (30) is arranged on the core (15) at the demolding station (3) in a position covered by the second mold cavity (23) at the second molding station (2).

17. The method according to claim 14, wherein the stripper (30) is slidingly moved onto the core (15) towards a first end (16) of the core (15) from its position at the first molding station (1) to its position at the second molding station (2) and from its position at the second molding station (2) to its position at the demolding station (3).

18. The method according to claim 14, wherein neither the first plastic material nor the second plastic material contacts the inner surface of the stripper during the manufacturing of the plastic hollow part.

* * * * *